US010441332B2

(12) United States Patent
Sands (10) Patent No.: US 10,441,332 B2
(45) Date of Patent: Oct. 15, 2019

(54) MEDIAL DISTAL FEMUR BONE PLATE SYSTEM

(71) Applicant: Stryker European Holdings I, LLC, Kalamazoo, MI (US)

(72) Inventor: Steven S. Sands, Edmond, OK (US)

(73) Assignee: Stryker European Holdings I, LLC, Kalamazoo, MI (US)

( * ) Notice: Subject to any disclaimer, the term of this patent is extended or adjusted under 35 U.S.C. 154(b) by 77 days.

(21) Appl. No.: 15/605,216

(22) Filed: May 25, 2017

(65) Prior Publication Data
US 2017/0258504 A1  Sep. 14, 2017

Related U.S. Application Data (63) Continuation of application No. 14/314,656, filed on Jun. 25, 2014, now abandoned.

(60) Provisional application No. 61/957,196, filed on Jun. 26, 2013.

(51) Int. Cl.
*A61B 17/80* (2006.01)
(52) U.S. Cl.
CPC ................. *A61B 17/8061* (2013.01)
(58) Field of Classification Search
CPC .............. A61B 17/746; A61B 17/8061; A61B 17/8052; A61B 17/8057; A61B 17/809
See application file for complete search history.

(56) References Cited

U.S. PATENT DOCUMENTS

| 5,674,222 | A | 10/1997 | Berger et al. |
| 7,951,176 | B2 | 5/2011 | Grady, Jr. et al. |
| 8,267,972 | B1 | 9/2012 | Gehlert |
| 2006/0004361 | A1 | 1/2006 | Hayeck et al. |
| 2006/0200163 | A1 | 9/2006 | Roger et al. |
| 2008/0300637 | A1 | 12/2008 | Austin et al. |
| 2010/0318086 | A1* | 12/2010 | Winemaker .......... A61B 17/683 606/70 |

FOREIGN PATENT DOCUMENTS

| EP | 0491983 B1 | 3/1996 |
| EP | 1 250 892 A2 | 10/2002 |
| EP | 2147647 A1 | 1/2010 |
| EP | 2389884 A1 | 11/2011 |
| EP | 1667590 B1 | 11/2012 |
| WO | 2011126590 A2 | 10/2011 |

OTHER PUBLICATIONS

International Search Report for PCT/US14/00152 dated Oct. 6, 2014.

* cited by examiner

*Primary Examiner* — Olivia C Chang
(74) *Attorney, Agent, or Firm* — Lerner, David, Littenberg, Krumholz & Mentlik, LLP (57) ABSTRACT

The current invention comprises a bone plate and method of use contoured to fit above the medial epicondyle that provides numerous apertures for fixation to the distal femur as desired with an offset screw design in shaft to allow location of screws around a nail or other feature and may also allow for attachment in conjunction with a lateral distal plate and or an extension plate that may cover the medial condyle.

19 Claims, 8 Drawing Sheets

MEDIAL DISTAL FEMUR BONE PLATE SYSTEM

CROSS-REFERENCE TO RELATED APPLICATIONS

The present application is a continuation of U.S. patent application Ser. No. 14/314,656, filed Jun. 25, 2014, which claims the benefit of U.S. Provisional Patent Application No. 61/957,196, filed Jun. 26, 2013, the disclosures of which are hereby incorporated herein by reference.

FIELD OF THE INVENTION

The present invention relates generally to surgical devices, system and method for internal fixation of fractures and non-unions of bones such as the femur. More particularly, the present invention provides a bone plating system for distal femur fractures and non-unions generally utilizing a specifically contoured bone plate or plates that fit to a corresponding specific portion or portions of the lower extremity of the femur.

DESCRIPTION OF THE KNOWN PRIOR ART

As known, the femur is the only bone in the thigh of humans and is the longest, heaviest and by most measures the strongest bone in the human body. The femur or thighbone is the most proximal bone of the leg in tetrapod vertebrates capable of walking or jumping and is categorized as a long bone and comprises a diaphysis, the shaft or body and two epiphyses that articulate with adjacent bones in the hip and knee. The femur is typically discussed as three general portions: the upper or proximal region, the middle portion referred to as the body or shaft, and the lower region often referred to as the distal femur, including the distal metaphysis and two condyles.

The lower extremity of the femur or distal extremity is larger than the upper extremity. It is somewhat cuboid in form, but its transverse diameter is greater than its antero-posterior. It consists of two oblong eminences known as the condyles.

Anteriorly, the condyles are slightly prominent and are separated by a smooth shallow articular depression called the patellar trochlea. Posteriorly, they project considerably and a deep notch, the intercondylar fossa of femur, is present between them. The lateral condyle is the more prominent and is the broader both in its antero-posterior and transverse diameters. The medial condyle is the longer and, when the femur is held with its body perpendicular, projects to a lower level. When, however, the femur is in its natural oblique position the lower surfaces of the two condyles lie practically in the same horizontal plane. The condyles are not quite parallel with one another; the long axis of the lateral is almost directly antero-posterior, but that of the medial runs backward and medialward. Their opposed surfaces are small, rough, and concave, and form the walls of the intercondyloid fossa. This fossa is limited above by a ridge, the intercondyloid line, and below by the central part of the posterior margin of the patellar surface. The posterior cruciate ligament of the knee joint is attached to the lower and front part of the medial wall of the fossa and the anterior cruciate ligament to an impression on the upper and back part of its lateral wall.

The articular surface of the lower end of the femur occupies the anterior, inferior, and posterior surfaces of the condyles. Its front part is named the patellar trochlea and articulates with the patella. It presents a median groove, which extends downward to the intercondyloid fossa and two convexities, the lateral of which is broader, more prominent, and extends farther upward than the medial.

Each condyle is surmounted by an elevation, the epicondyle. The medial epicondyle is a large convex eminence to which the tibial collateral ligament of the knee joint is attached. At its upper part is the adductor tubercle and behind it is a rough impression, which gives origin to the medial head of the gastrocnemius. The lateral epicondyle, which is smaller and less prominent than the medial, gives attachment to the fibular collateral ligament of the knee-joint.

The knee is the largest weight-bearing joint in the body. The distal femur makes up the top part of the knee joint. The upper part of the shinbone or tibia supports the bottom part of the knee joint. The ends of the femur are covered in a smooth, slippery substance called articular cartilage. This cartilage protects and cushions the bone when bending and straightening the knee.

The body of the femur or shaft is long, slender and almost cylindrical in form and connects to the distal portion. It is a little broader above than in the center, broadest and somewhat flattened from before backward below. It is slightly arched, so as to be convex in front, and concave behind, where it is strengthened by a prominent longitudinal ridge, the linea aspera that diverges proximal and distal as the medial and lateral ridge.

Fractures of the thighbone that occur just above the knee joint are called distal femur fractures. The distal femur is where the bone flares out like an upside-down funnel. Fractures of the distal femur most commonly occur in two patient types that being younger people typically considered under age 50 and the elderly.

Distal femur fractures in younger patients are usually caused by high-energy injuries, such as falls from significant heights or motor vehicle collisions. Because of the forceful nature of these fractures, many patients also have other injuries, often of the head, chest, abdomen, pelvis, spine, and other limbs.

Elderly people with distal femur fractures typically have poor bone quality. As we age, our bones get thinner. Bones can become very weak and fragile. A lower-force event, such as a fall from standing, can cause a distal femur fracture in an older person who has weak bones. Although these patients do not often have other injuries, they may have concerning medical problems, such as conditions of the heart, lungs, and kidneys, and diabetes.

Distal femur fractures vary. The bone can break straight across often referred to as a transverse fracture or into many pieces often referred to as a comminuted fracture. Sometimes these fractures extend into the knee joint and separate the surface of the bone into a few or many parts. These types of fractures are called intra-articular. Because they damage the cartilage surface of the bone, intra-articular fractures can be more difficult to treat.

Distal femur fractures can be closed, meaning the skin is intact, or can be open. An open fracture is when a bone breaks in such a way that bone fragments stick out through the skin or a wound penetrates down to the broken bone. Open fractures often involve much more damage to the surrounding muscles, tendons, and ligaments. They have a higher risk for complications and take a longer time to heal.

When the distal femur breaks, both the hamstrings and quadriceps muscles tend to contract and shorten. When this happens, the bone fragments change position and become difficult to line up with a cast.

It is known in distal humerus fractures to utilize medial and lateral column plating. It is also known in proximal tibia fractures to utilize medial and lateral column plating. However, distal femur fractures are typically treated with just lateral plates. Lateral locking plates are well established and generally have a good track record, but lateral plate failure is also well known.

When lateral locking plates fail, it is common to go varus or apex lateral angulation of the distal segment of a bone. Furthermore, lateral plates have no medial column support or buttress. When varus failure occurs, medial buttress plating is often done and the current prior art option is to bend a straight plate and hope it fits well.

Although numerous advancements have occurred in the field of bone plates in general, the prior art still has failed to bridge the gap between the needs of medical professionals treating distal femur issues and the ever increasing demand. Therefore, an extensive opportunity for design advancements and innovation remains for medial distal femur plate devices, systems, and methods where the prior art fails or is deficient.

SUMMARY OF THE INVENTION

In general, the present invention is a new and improved surgical device, system, and method which provides a bone plate for the treatment of fractures and non-unions of femurs where the prior art fails. The present invention generally provides a contoured plate or plates specifically contoured to correspond with associated locations on the medial distal femur.

Without the intention of limitation, the invention may generally comprise a plate or plates adapted to conform to the medial area of the distal femur from generally near the medial epicondyle and generally up the shaft of the femur. The plate may include numerous apertures for fixation to the distal femur as desired such as but not limited to an offset screw design along the shaft to allow location of screws around a nail or other feature. A preferred construction may allow for the placement of screws through the plate into the shaft of the femur, the placement of screws through the plate generally into the lateral condyle, the placement of screws through the plate generally into the medial condyle and so forth. It is understood that the current invention may allow for fixation for multiple sites. The medial distal plate may be used in conjunction with a lateral distal plate. It is further contemplated to provide an extension plate to generally cover the medial condyle.

Furthermore, the invention may include a method for utilizing a medial distal plate such as but not limited to making an incision approximately 15 cm from the knee joint proximally. Deep fascia may be split in line with the skin incision and may include saphenous vein and nerve retracted either anteriorly or posteriorly. Vastus medialis may be dissected off of the intermuscular or IM septum. Subperiosteal dissection may expose distal femur and to be noted is that the femoral vessels may be safely out of the fixation zone.

In this respect, before explaining at least one embodiment of the invention in detail, it is to be understood that the invention is not limited in this application to the details of construction and to the arrangement of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting. As such, those skilled in the art will appreciate that the conception, upon which this disclosure is based, may readily be utilized as a basis for the designing of other structures, methods and systems for carrying out the several purposes of the present invention. It is important, therefore that the claims be regarded as including such equivalent constructions insofar as they do not depart from the spirit and scope of the present invention.

Accordingly, titles, headings, chapter names, classifications and overall segmentation of the application in general should not be construed as limiting. Such are provided for overall readability and not necessarily as literally defining text or material associated therewith.

Further, the purpose of the foregoing abstract is to enable the U.S. Patent and Trademark Office and the public generally, and especially the scientist, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new and improved medial distal femur bone plate devices, system and method of using the same that provides greater ease of use, patient comfort, and function to a wide range of uses associated with the fractures and non-unions.

It is a further object of the present invention to provide a new and improved medial distal femur bone plate devices, system and method of using the same, which is of a robust design, as well as be easily and efficiently manufactured.

An even further object of the present invention is to provide a new and improved medial distal femur bone plate devices, system and method of using the same, which is of a more durable and reliable construction than that of the existing known art.

Still another object to the present invention is to provide a new and improved medial distal femur bone plate devices, system and method of using the same, which is susceptible of a low cost of manufacture with regard to both materials and labor, which accordingly is then susceptible of competitive prices of sale to the public, thereby making such economically available to those in need.

Another object of the present invention is to provide a new and improved medial distal femur bone plate devices, system and method of using the same, which provides some of the advantages of the prior art, while simultaneously overcoming some of the disadvantages normally associated therewith.

Yet another object of the present invention is to provide a new and improved medial distal femur bone plate devices, system and method of using the same that provides multiple fixation options as well as multiple treatment location options.

Still further, it is an object of the present invention to provide a new and improved medial distal femur bone plate devices, system and method of using the same that will allow the medical professional to always have a readily available bone plate system that allows a surgeon to plate around previously inserted objects such as but not limited to intramedullary nail, total knee arthroplasty and so forth.

It is a further object of the present invention to provide a new and improved medial distal femur bone plate devices, system and method of using the same that may be used in conjunction with a lateral distal femur plate and other medial lateral plates.

These together with other objects of the invention, along with the various features of novelty, which characterize the invention, are pointed out with particularity in the claims annexed to and forming a part of this disclosure. For a better understanding of the invention, its operating advantages and the specific objects attained by its uses, reference would be had to the accompanying drawings and descriptive matter in which there are illustrated preferred embodiments of the invention.

BRIEF DESCRIPTION OF THE DRAWINGS AND PICTORIAL ILLUSTRATIONS

The invention will be better understood and objects other than those set forth above will become apparent when consideration is given to the following detailed description thereof. Such description makes reference to the annexed pictorial illustrations, graphs, drawings, and appendices.

DETAILED DESCRIPTION OF THE PREFERRED EMBODIMENTS

Figure 1:
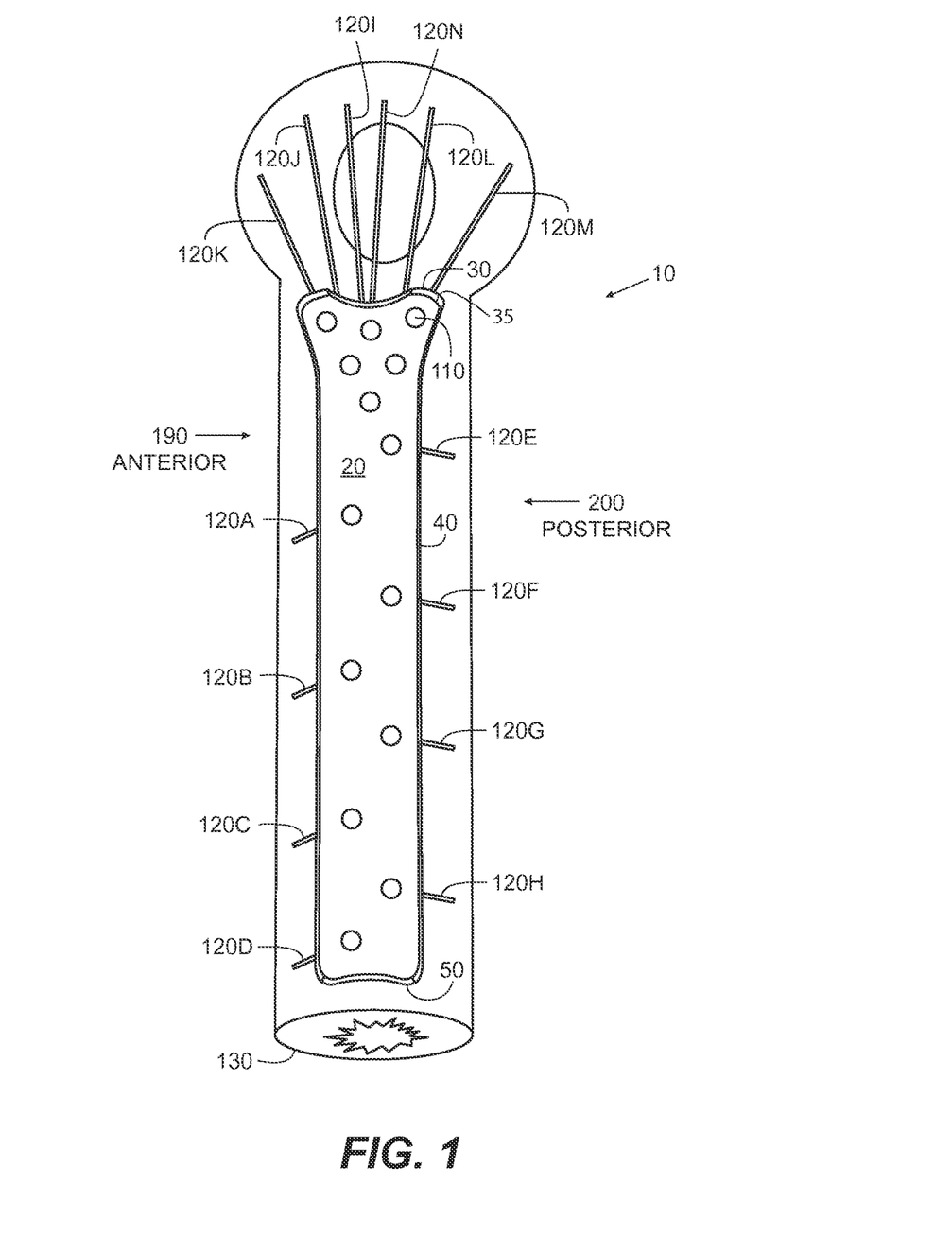
FIG. 1 is a general top view depiction of a preferred embodiment of the invention attached to a femur.

Referring now to the drawings, wherein like reference numerals designate corresponding structure throughout the views, and referring in particular to FIG. 1, reference numeral 10 generally refers to a new and improved medial distal femur bone plate devices, system and method of using the same hereinafter referred to as "invention 10" or "invention", in accordance with a preferred embodiment of the current invention.

Invention 10 generally contemplates, as discussed further below, a pre-contoured plate designed for fixation of the femur shaft and distal femur that is applied to the medial side of the femur. The plate may include holes that may have threads and a shape to accommodate locking screws, non-locking screws, cables, pins, trochars, guides, buttons, and or extensions that may be located along the entire length of the plate. Invention 10 contemplates additional holes of varying sizes and shapes along the plate for accommodating other bone fixation devices such as wires, pins, buttons, cables, extensions, guides, and so forth. The distal portion of the plate may match the shape of the medial portion of the medial condyle. The screw holes along the distal portion of the plate may be designed to accommodate screws for fixation of the distal femur, including the medial condyle, lateral condyle, intercondylar trochlea, and metaphyseal portion of the femur. The shaft portion of the plate may be essentially straight in the coronal plane with a slight curve in the sagittal plane to match the natural sagittal curve of the femur shaft.

The screw holes along the shaft portion of the plate may accommodate screws for affixing the plate to the medial femur shaft and/or for fixation of fractures extending proximal to the distal femur along the shaft of the femur. There may be a transitional portion of the plate that will curve between the shaft portion and the distal portion. The curve of this transitional zone may contour to the distal medial metaphyseal portion of the femur. There may be screw holes or other holes placed along this transitional zone of the plate More in particular, invention 10 may generally include plate 20 having a first end 30, a shaft and or middle 40, a second end 50, a top surface 60, a bottom surface 70, a width 80, a length 90, and a thickness 100. It is understood that plate 20 may have many configurations, shapes, sizes and so forth and the current invention should not be considered limited to the illustrations. It is also contemplated that first end 30 may include a flared portion 35 generally making first end 30 wider than second end 50 and middle 40. The illustrations generally depict a preferred embodiment and it is understood that numerous other embodiments are contemplated.

Figure 6:
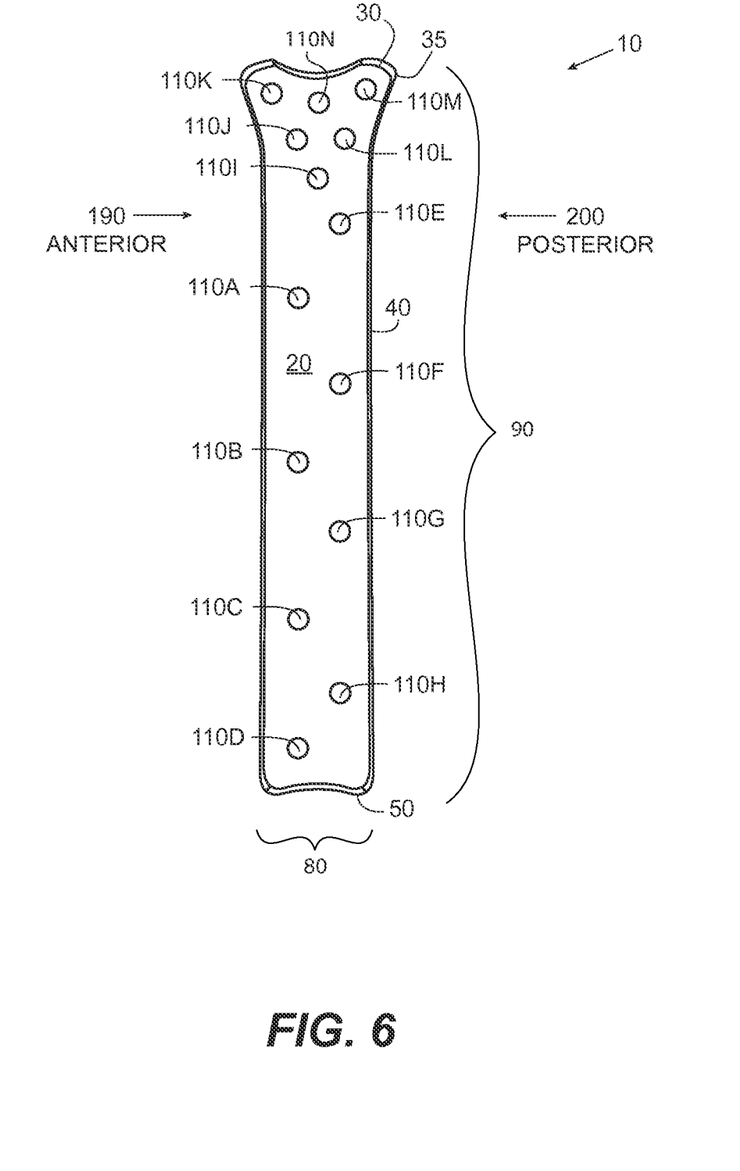
FIG. 6 is a general top view depiction of a preferred embodiment of the invention.

Referring to the illustration and more in particular to FIG. 6, in a preferred embodiment length 90 may be about 15 centimeters. It is understood that length 90 may be shorter or longer. In a preferred embodiment, width 80 may be about 18 mm around second end 50 and or middle 40 and 35 mm around first end 30 and flare 35. It is also understood that width 80 may be shorter or longer. In a preferred embodiment, thickness 100 may be about 5 mm. It is understood that thickness 100 may be greater or lesser. It is also understood that plate 20 may be generally sized to generally adapt for larger people, smaller people, and so forth and contoured accordingly. Invention 10 may include a surgery kit with numerous sizes of bone plate 20 as desired for treating individuals.

Invention 10 may include numerous holes or aperture 110 as will be discussed further below. It is also understood that invention 10 may utilize bone anchors 120 such as but not limited to known cannulated locking screws as indicated for certain types of fractures and non-unions of the proximal femur. Invention 10 may also utilize other bone anchors 120 such as non-cannulated non-locking screws, non-cannulated locking screws, variable angle locking screws, fixed angle nails, pins, blades, cables, wires and combination thereof. It is also understood that bone anchors 120 generally cooperate with plate 20 apertures 110 to secure the various bone anchor 120 to the femur 130 as will also be discussed in greater detail below.

Figure 7:
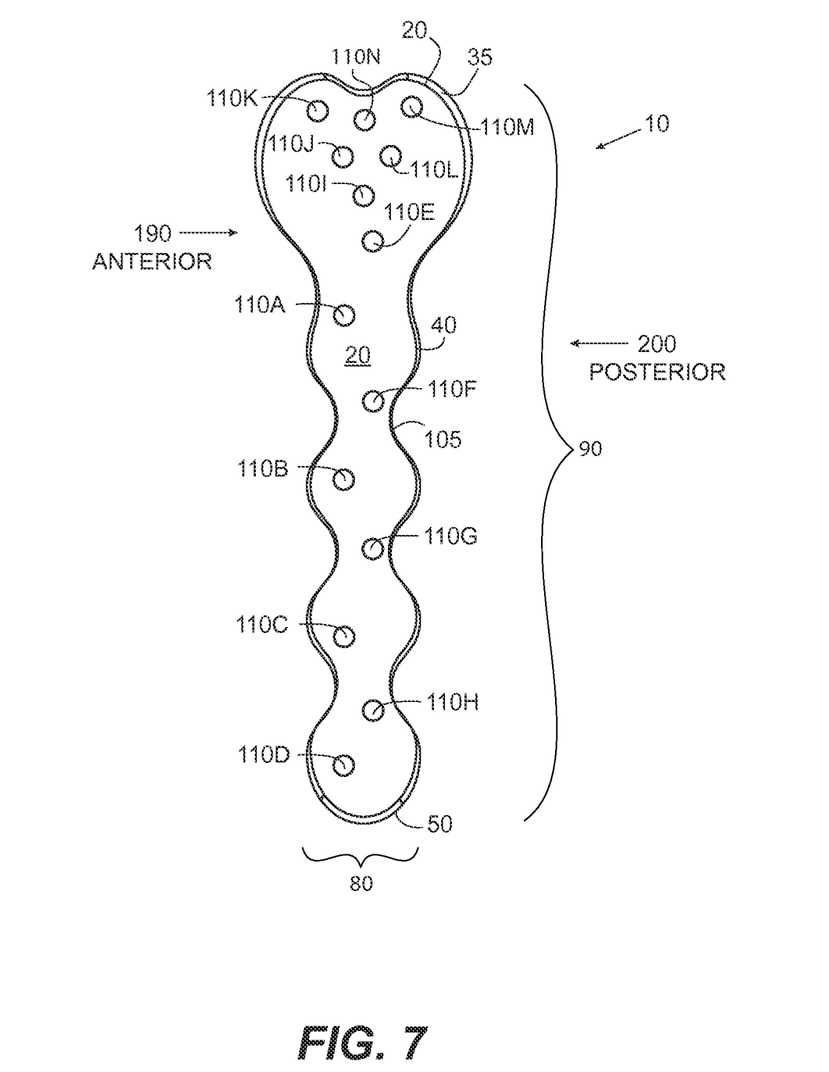
FIG. 7 is another general top view depiction of a preferred embodiment of the invention.

Again referring to the illustration and more in particular to FIG. 7, invention 10 contemplates utilizing scalloped edges 105. It is contemplated that plate 20 may have a configuration wherein irregular edges may be included such that a flare is created out around the holes 110. It is understood that numerous configurations of scalloped edges 105 are contemplated and the illustration should not be considered to limit invention 10 to the depicted.

Bone plate 20 may be made from metal such as but not limited to stainless steel, titanium, composite materials, combinations thereof, and so forth. It is understood that plate 20 may be made of other materials other than metal. Bone anchors 120 are known in the art and may be of numerous materials.

Figure 2:
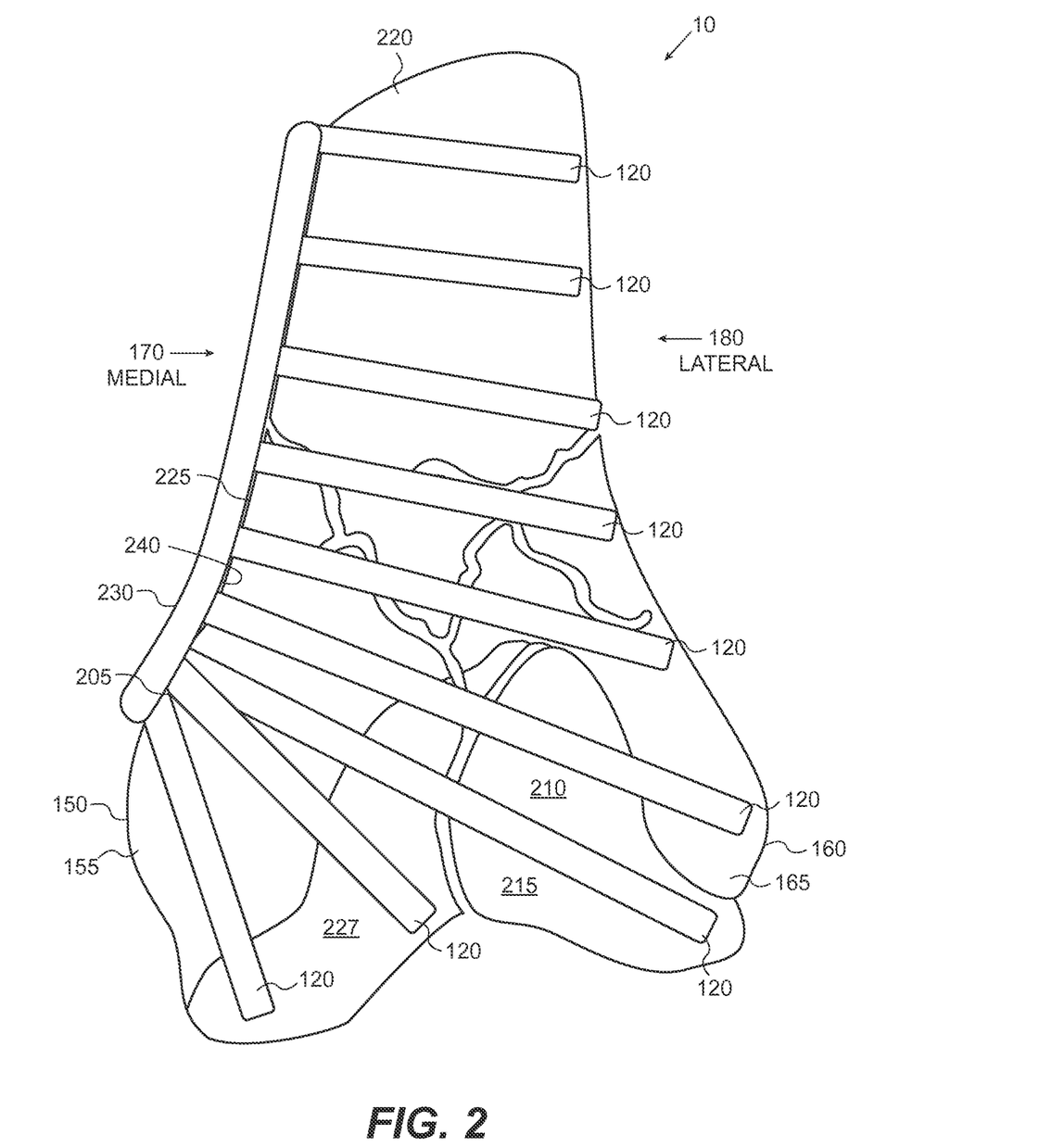
FIG. 2 is a general side view depiction of a preferred embodiment of the invention attached to a femur.

Referring to the illustration in general and more in particular to FIG. 2, It is understood that femur 130 has a distal end 140, a medial epicondyle 150, a medial condyle 155, a lateral epicondyle 160, a lateral condyle 165, a medial aspect or side 170, a lateral aspect or side 180, an anterior aspect or side 190, a posterior aspect or side 200, adductor magnus tubercle 205, a patellar surface 210, intercondylar trochlear region 215, main body or shaft 220, metaphyseal bone portion 225 and so forth.

It is understood that the articular surface 227 of the lower or distal end 140 femur 130 occupies the anterior, inferior, and posterior surfaces of the condyles. Its front part is named the patellar surface 210 and articulates with the patella.

Invention 10 contemplates plate 20 bottom surface 70, thickness 100, and or top surface 60 are generally contoured to adapt to femur 130 distal end 140 medial aspect 170. Bottom surface 70 may be generally curved as depicted although invention 10 contemplates numerous contouring and or curvature.

Invention 10 contemplates plate 20 generally to be positioned such that first end 30 does not extend past medial condyle 155, but rather ends on or about medial epicondyle 150, articular surface 227 of medial condyle 155 and or adductor magnus tubercle 205 as generally depicted. It is also contemplated that plate 20 may extend past the aforementioned. Second end 50 may generally be positioned on shaft 220 of femur 130 and may have a varying length 90. Plate 20 second end 50 may generally be positioned along femur 130 shaft 220 and be limited in length 90 and generally positioning by the vascular structures crossing the medial aspect 170 femur 130 from anterior aspect 190 to posterior aspect 200 such as femoral artery and or femoral vein. It is also contemplated that length 90 of bone plate 20 generally may be the same as the length between shaft 220 and same medial epicondyle 150 of femur 130 in a preferred construction.

Plate 20 may extend posteriorly to the level of the adductor magnus tubercle 205 and posterior aspect 200 to femur 130 shaft 220. Plate 20 may also extend anteriorly to the anterior-medial portion of femur 130 shaft 220 and medial and anterior-medial facet of the medial condyle 155 and medial epicondyle 150.

The present invention 10 contemplates providing plate 20 with apertures 110A, 110B, 110C, and 110D for generally positioning bone anchors 120A, 120B, 120C, and 120D generally anterior aspect 190 and on shaft 220. The present invention 10 also contemplates providing plate 20 with apertures 110E, 110F, 110G, and 110H for generally positioning bone anchors 120E, 120F, 120G, and 120H generally posterior aspect 200 on shaft 220. It is further contemplated these bone anchors 120 are generally perpendicular to plate 20. Although it is understood that closer to the medial epicondyle 150 the angle may change more so and the bone anchors 120 may engage the region below the area known commonly as the shaft 220 such as but not limited to medial condyle 155, lateral condyle 165, and so forth.

Holes or apertures 110 may be threaded, angled, and so forth to cooperate with bone anchors 120. A preferred embodiment may be where bone anchors 120 head finish generally flush with bone plate 20 top surface 60. By example, holes or apertures 110 may further include a recessed portion for providing a screw head to finish flush generally inside bone plate 20.

Figure 5:
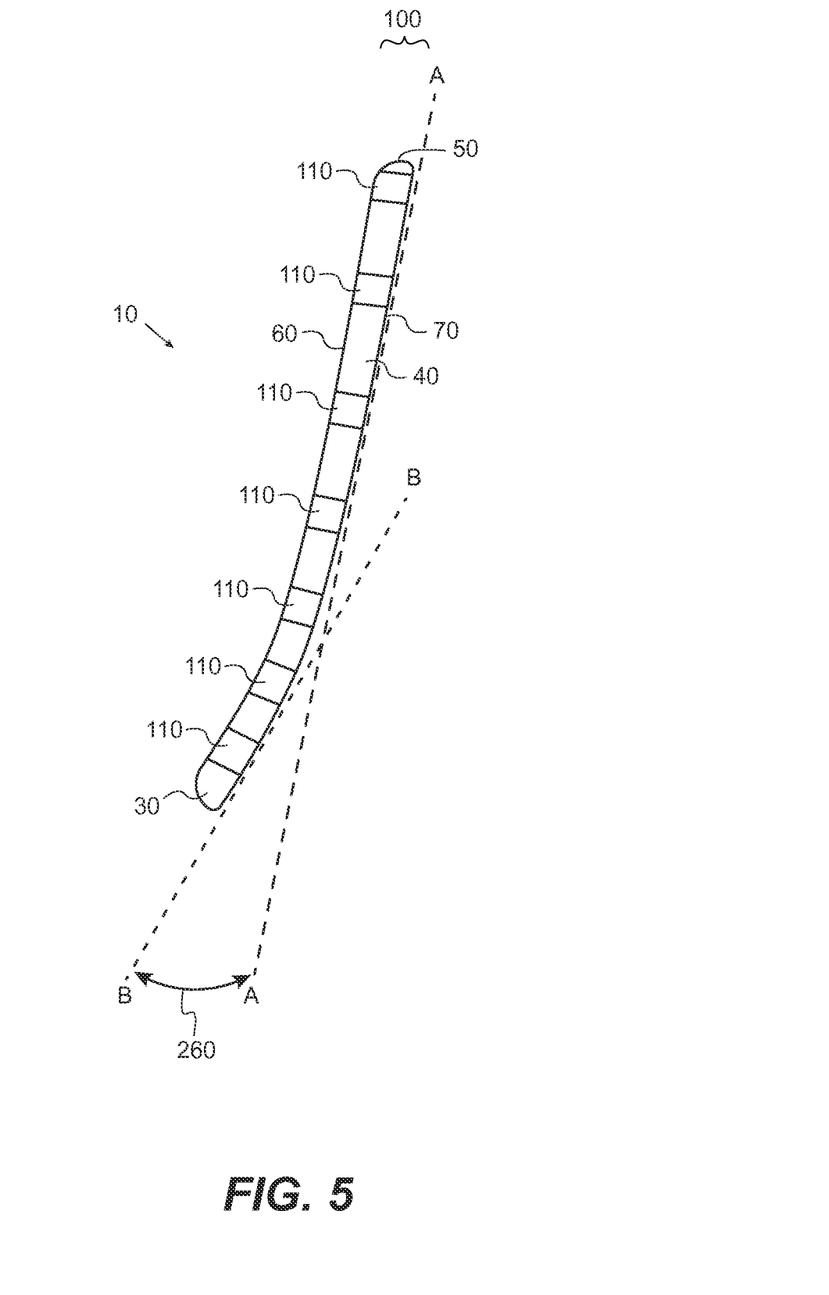
FIG. 5 is a general side view depiction of a preferred embodiment of the invention.

Referring to the illustration and more in particular to FIGS. 2 and 5, it is understood that plate 20 has generally an angle or curve 230 wherein plate 20 first end 30 is generally flush along femur 130 corresponding angle or curve 240 and generally positioned above the medial epicondyle 150. Curve 230 may be generally angled as defined as angle 260 between Line AA which may generally lay along and parallel with plate 20 bottom surface 70 at second end 50 and Line BB, which may generally lay along and parallel with first end 30. Angle 260 may generally be 20 degrees although it is contemplated that angle 260 may be greater or smaller.

Still further, invention 10 contemplates utilizing plate 20 with apertures 110I, 110J, 110K, 110L, 110M, and 110N for generally positioning bone anchors 120I, 120J, 120K, 120L, 120M, and 120N along plate 20 curve 230. These bone anchors 120 may generally be longer such that they engage the medial condyle 155 and lateral condyle 165.

It is contemplated that bone anchors 120 may generally be placed along plate 20 first end 30, shaft and or middle 40, second end 50. It is further contemplated that bone anchors 120 such as but not limited to screws generally positioned on first end 30 plate 20 angle or curve 230 may be pointed in such a trajectory as to gain fixation in the medial condyle 155, lateral condyle 165, intercondylar trochlear region 215, and/or the metaphyseal bone 225 of the distal end 140 femur 130.

Bone anchors 120 may be directed around previously-placed hardware such as the femoral component of total knee arthroplasty, intramedullary implants, plates, screws, or other implanted hardware. In a preferred embodiment, bone anchors 120 may be positioned with plate 20 such that bone anchors 120 do not touch.

Figure 3:
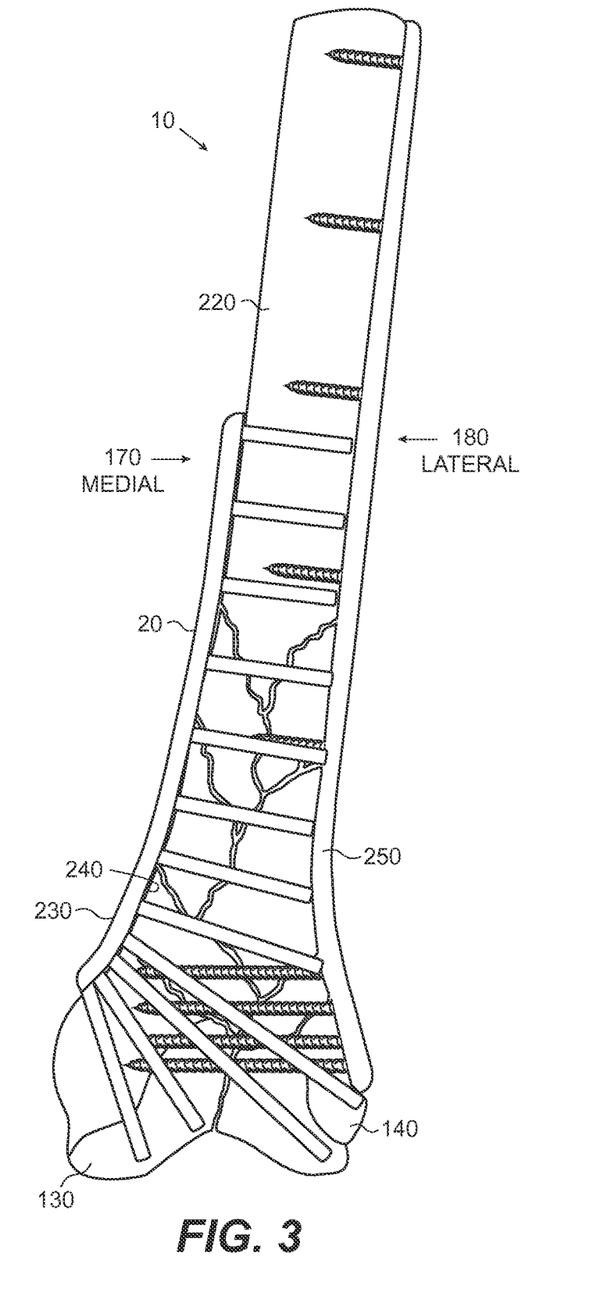
FIG. 3 is a general side view depiction of a preferred embodiment of the invention attached to a femur and also generally depicting a distal lateral plate.

Referring to the illustrations again and more in particular to FIG. 3, in a preferred embodiment, invention 10 may include use of a lateral plate 250. It is understood that lateral plate 250 may be of a similar construction as plate 20 but corresponding to the lateral distal femur accordingly.

Figure 8:
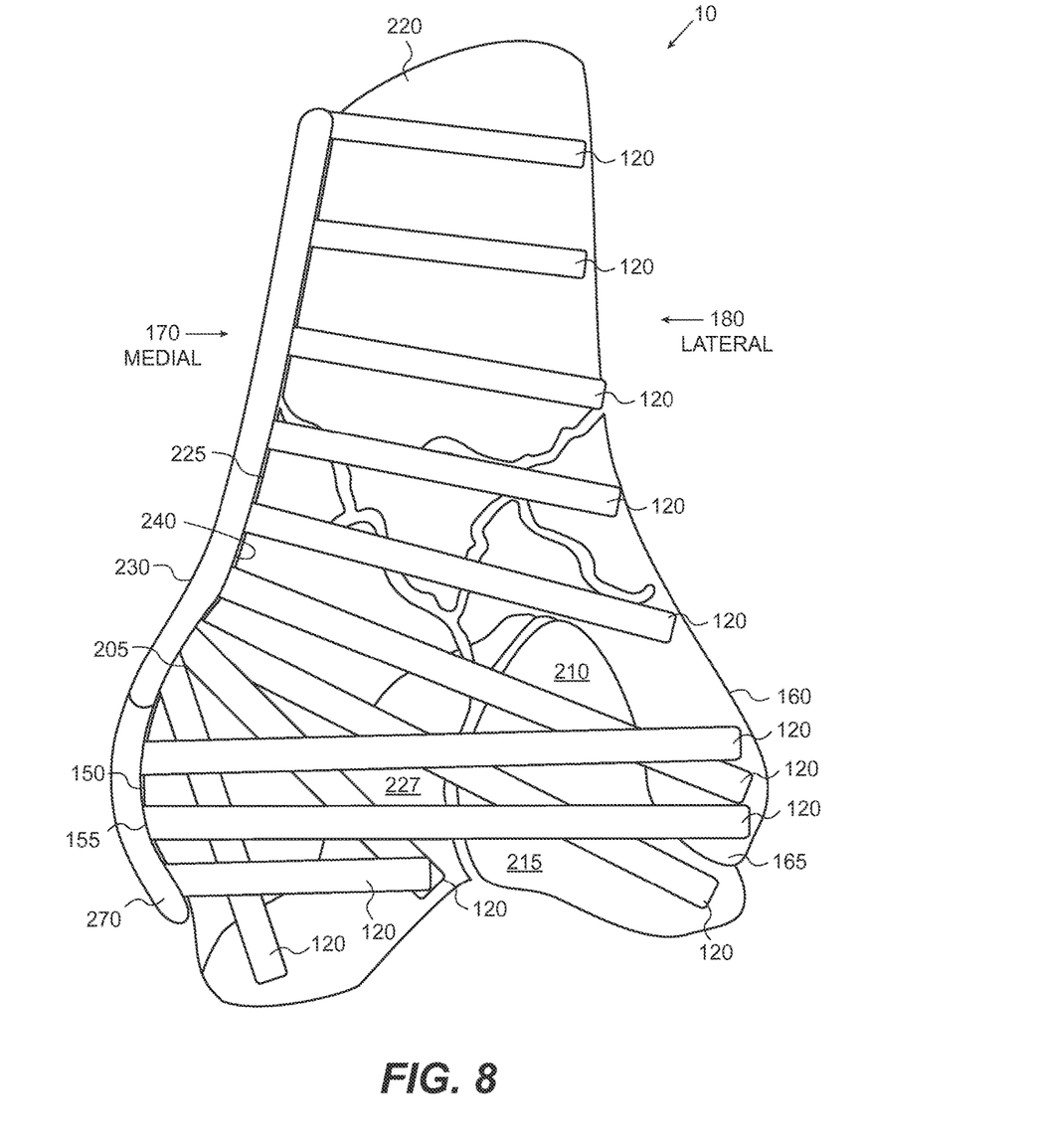
FIG. 8 is another general side view depiction of a preferred embodiment of the invention attached to a femur.

Once again referring to the illustrations and more in particular to FIG. 8, in a preferred construction, invention 10 may utilize an extension plate 270 that generally covers medial condyle 155 and may or may not abut plate 20 first end 30. It is contemplated that extension plate 270 may include apertures 110 for bone anchors 120.

Figure 4:
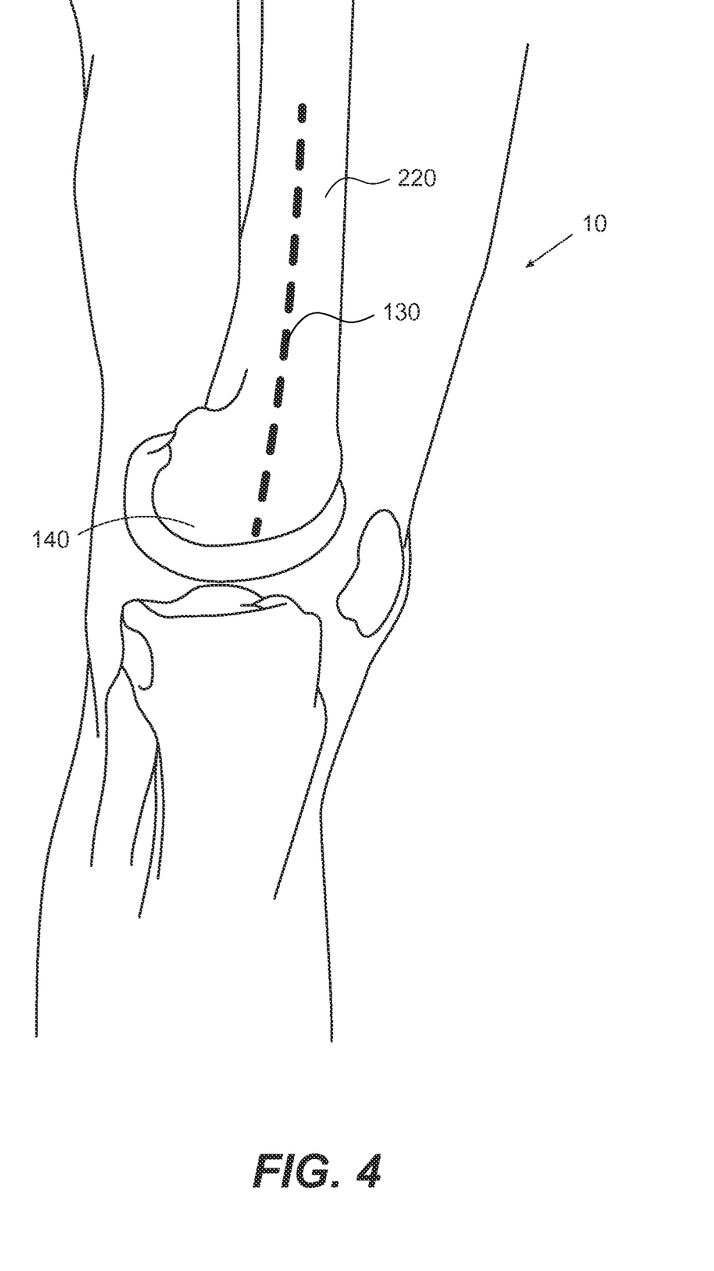
FIG. 4 is a general depiction of a method for making and locating an incision in accordance with a preferred embodiment of the invention

Once again referring to the drawings in general and more specifically to FIG. 4, invention 10 may include a method for utilizing a medial distal plate 20 such as but not limited to making an incision approximately 15 cm from the knee joint proximally. Deep fascia may be split in line with the skin incision and may include saphenous vein and nerve retracted posteriorly. Vastus medialis may be dissected off of the intermuscular or IM septum. Subperiosteal dissection may expose distal femur 130 and to be noted is that the femoral vessels may be safely out of the fixation zone.

Invention 10 may be utilized for the direct fixation of the medial aspect 170 distal end 140 of femur 130 and medial aspect 170 femur 130 shaft 220, primary fixation of distal end 140 femur 130 fractures, primary fixation of femur 130 shaft 220 fractures, secondary (adjunct) fixation of distal end 140 femur 130 or femur 130 shaft 220 fractures in addition to intramedullary or lateral-based fixation, and so forth. Invention 10 may also be utilized with periprosthetic fractures including but not limited to above the femoral component of total knee arthroplasty, at the distal end of intramedullary implant in femur 130, above or below previously-placed femoral hardware, and so forth. It is also contemplated to be utilized with an out rigger as known in art for percutaneous fixation.

Possible indications may be primary fractures of femur 130 shaft 220 or distal end 140 femur 130, peri-prosthetic fractures of femur 130 shaft 220 or distal end 140 femur 130, non-united fractures of femur 130 shaft 220 and or distal end 140 femur 130 requiring primary or secondary medial aspect 170 fixation, and so forth.

It is therefore contemplated invention 10 may provide bone plate 20 for treating fractures and non-unions of distal femur 130 said femur 130 having shaft 220 with medial aspect 170, medial epicondyle 150, and a length defined as the distance between said shaft 220 with medial aspect 170 and said medial epicondyle 150 and wherein said length has curve 240; said bone plate 20 comprising top surface 60, bottom surface 70 for contacting said femur 130; one or more apertures 110 wherein said one or more apertures 110 pass through said top surface 60 and said bottom surface 70 and are configured to fix a bone anchor 120 through said top surface 60 and said bottom surface 70 to attach said bone plate 20 to said femur 130; first end 30 for attaching to said medial epicondyle 150; second end 50 for attaching to said shaft 220 with medial aspect 170; length 90 defined as the distance between said first end 30 and said second end 60 and said length 90 having curve 230 wherein said length 90 generally matches said length on said femur 130 and wherein said curve 230 generally matches said curve 240 of said length on said femur 130.

Accordingly, other implementations are within the scope of the following claims. Changes may be made in the combinations, operations, and arrangements of the various parts and elements described herein without departing from the spirit and scope of the invention.

I claim:

1. A method for internal fixation of fractures and non-unions of a distal femur comprising:
    contacting a distal end of a medial distal femur plate with a medial condyle of a femur;
    contacting a proximal end of the medial distal femur plate with the medial femur shaft;
    inserting a plurality of bone anchors through the medial distal femur plate and into a medial side of the femur such that the medial distal femur plate is secured to the femur exclusively by the plurality of bone anchors, wherein the step of inserting a plurality of bone anchors includes inserting at least one first bone anchor through a first aperture formed through the distal end of the medial distal femur plate and into a medial side of the femur, and inserting at least one second bone anchor through a second aperture formed through the proximal end of the medial distal femur plate and into the medial side of the femur.

2. A method for internal fixation of fractures and non-unions of a distal femur comprising:
    contacting a distal end of a medial distal femur plate with a medial condyle of a femur;
    contacting a proximal end of the medial distal femur plate with the medial femur shaft;
    inserting at least one first bone anchor through a first aperture formed through the distal end of the medial distal femur plate and into a medial side of the femur; and
    inserting at least one second bone anchor through a second aperture formed through the proximal end of the medial distal femur plate and into the medial side of the femur,
    wherein the distal end is wider than the proximal end and includes a first and a second flared portion, the first flared portion extending distally and anteriorly and the second flared portion extending distally and posteriorly such that the distal end conforms to a curvature of the medial condyle.

3. The method according to claim 2, wherein the step of contacting the distal end includes contacting the distal end of the medial distal femur plate to a magnus tubercle of the medial condyle.

4. The method according to claim 2, wherein the distal end is concave between the first and second flared portions.

5. The method according to claim 2, wherein a body of the medial distal femur plate is disposed between the proximal and the distal ends, the distal end extending medially and distally away from the body such that the distal end and the body define a curve conforming to the concave curvature of a medial surface of the distal femur.

6. The method according to claim 5, wherein the curve is less than or equal to 20 degrees.

7. The method according to claim 5, wherein the curve is more than 20 degrees.

8. The method according to claim 2, wherein at least one first bone anchor extends from the medial condyle into the lateral condyle such that a distal end of the first bone anchor is disposed within the lateral condyle.

9. The method according to claim 2, further comprising the step of attaching a lateral plate to a lateral side of the distal femur.

10. The method according to claim 2, wherein a length of the medial distal femur plate is at least 15 centimeters.

11. The method according to claim 2, wherein a length of the medial distal femur plate is less than 15 centimeters.

12. The method according to claim 2, where the medial distal femur plate is made from titanium.

13. The method according to claim 2, wherein the medial distal femur plate is made from stainless steel.

14. The method according to claim 2, wherein the top surface is at a distance of at least 5 millimeters from the bone contacting surface.

15. The method according to claim 2, wherein the top surface is at a distance of less than 5 millimeters from the bone contacting surface.

16. The method according to claim 2, wherein the distal end has a width of at least 35 millimeters.

17. The method according to claim 2, wherein the distal end has a width less than 35 millimeters.

18. The method according to claim 2, wherein the proximal end has a width of at least 18 millimeters.

19. The method according to claim 2, wherein the proximal end has a width of less than 18 millimeters.

* * * * *